United States Patent [19]

Fukasawa et al.

[11] Patent Number: 5,706,081
[45] Date of Patent: Jan. 6, 1998

[54] APPARATUS FOR INSPECTING SURFACE DEFECTS WITH REGULARLY REFLECTED LIGHT AND PERIPHERALLY SCATTERED LIGHT

[75] Inventors: Toshio Fukasawa; Masami Eishima; Shinichiro Nagai; Junichi Ono, all of Kanagawa, Japan

[73] Assignee: NSK Ltd., Tokyo, Japan

[21] Appl. No.: 852,702

[22] Filed: May 7, 1997

Related U.S. Application Data

[63] Continuation of Ser. No. 413,470, Mar. 28, 1995, abandoned.

[30] Foreign Application Priority Data

Mar. 28, 1994 [JP] Japan .................. 6-080956

[51] Int. Cl.$^6$ .................. G01N 21/00; G01N 21/84
[52] U.S. Cl. .................. 356/237; 356/431; 250/559.4; 250/559.46
[58] Field of Search .................. 356/394, 237, 356/431; 250/559.04, 559.06, 559.4–559.42, 559.45–559.46, 559.48

[56] References Cited

U.S. PATENT DOCUMENTS

| | | | |
|---|---|---|---|
| 5,105,092 | 4/1992 | Natsubori et al. | 250/559.06 |
| 5,278,635 | 1/1994 | Ono et al. | 356/237 |
| 5,363,187 | 11/1994 | Hagiwara et al. | 356/237 |

*Primary Examiner*—Frank G. Font
*Assistant Examiner*—Jason D. Vierra-Eisenberg
*Attorney, Agent, or Firm*—Sughrue, Mion, Zinn, Macpeak & Seas, PLLC

[57] ABSTRACT

Virtually all of the light reflected from an object to be inspected is made incident upon a focusing lens 7, a quantity of light in a regularly reflected light region on an plane P1 where an image is formed by a lens 7 is detected by a photodiode 8, while a quantity of light in a peripherally scattered light region is detected by a photodiode 9. If the quantity of light received (VDET1) in the regularly reflected light region is lower than a first reference value (VREF1) (S1=1), and the quantity of light received (VDET2) in the peripheral scattered light region is higher than a second reference value (VREF2) (S2=1), a determination is made that a defect is present.

10 Claims, 6 Drawing Sheets

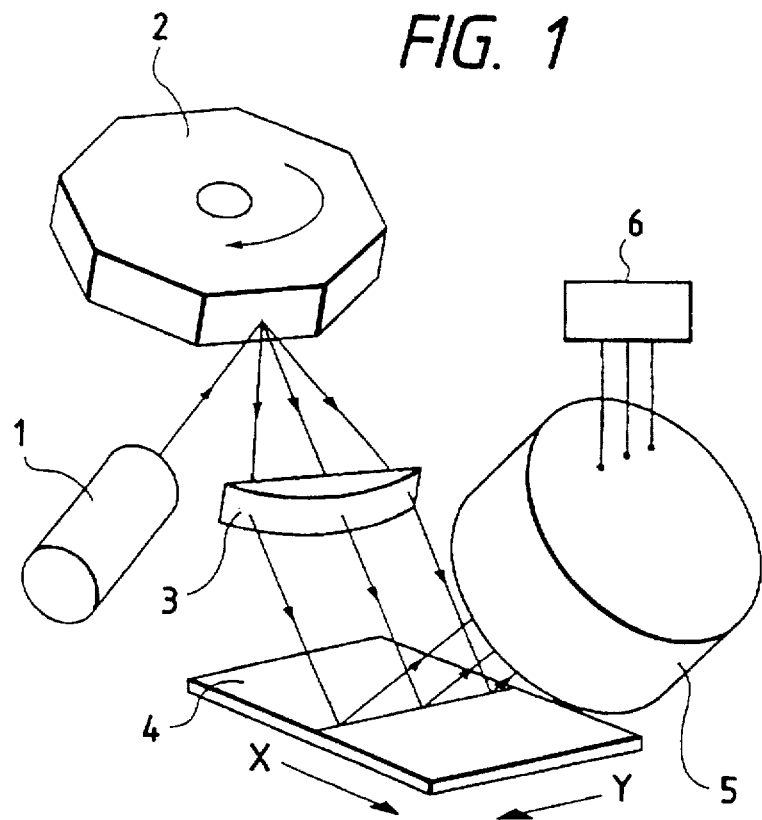
FIG. 1
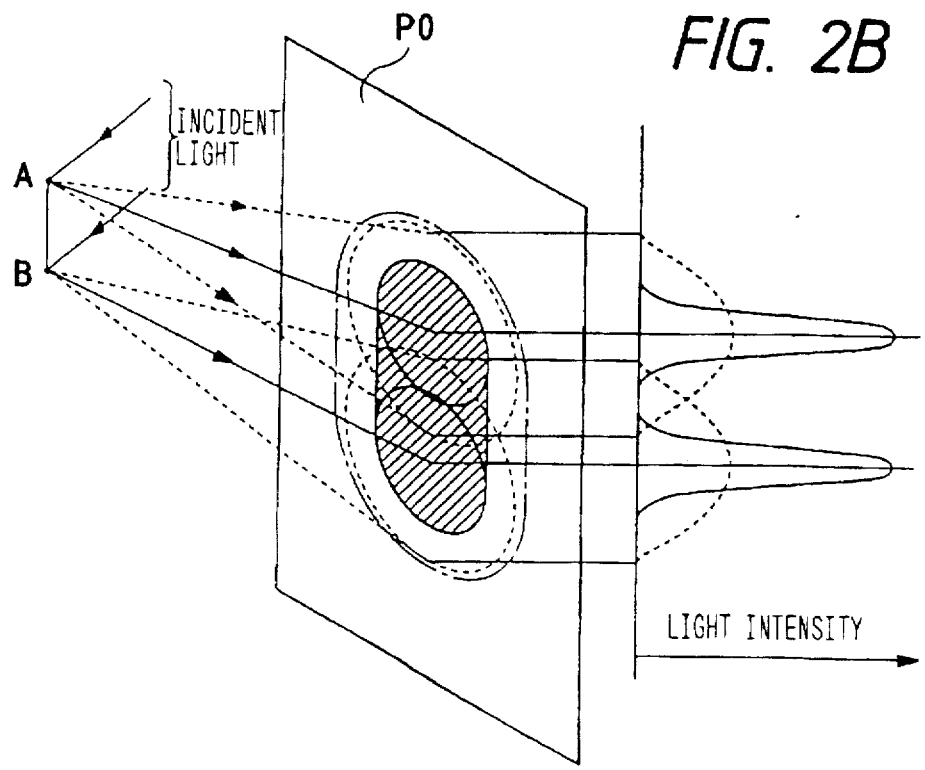
FIG. 2A
FIG. 2B

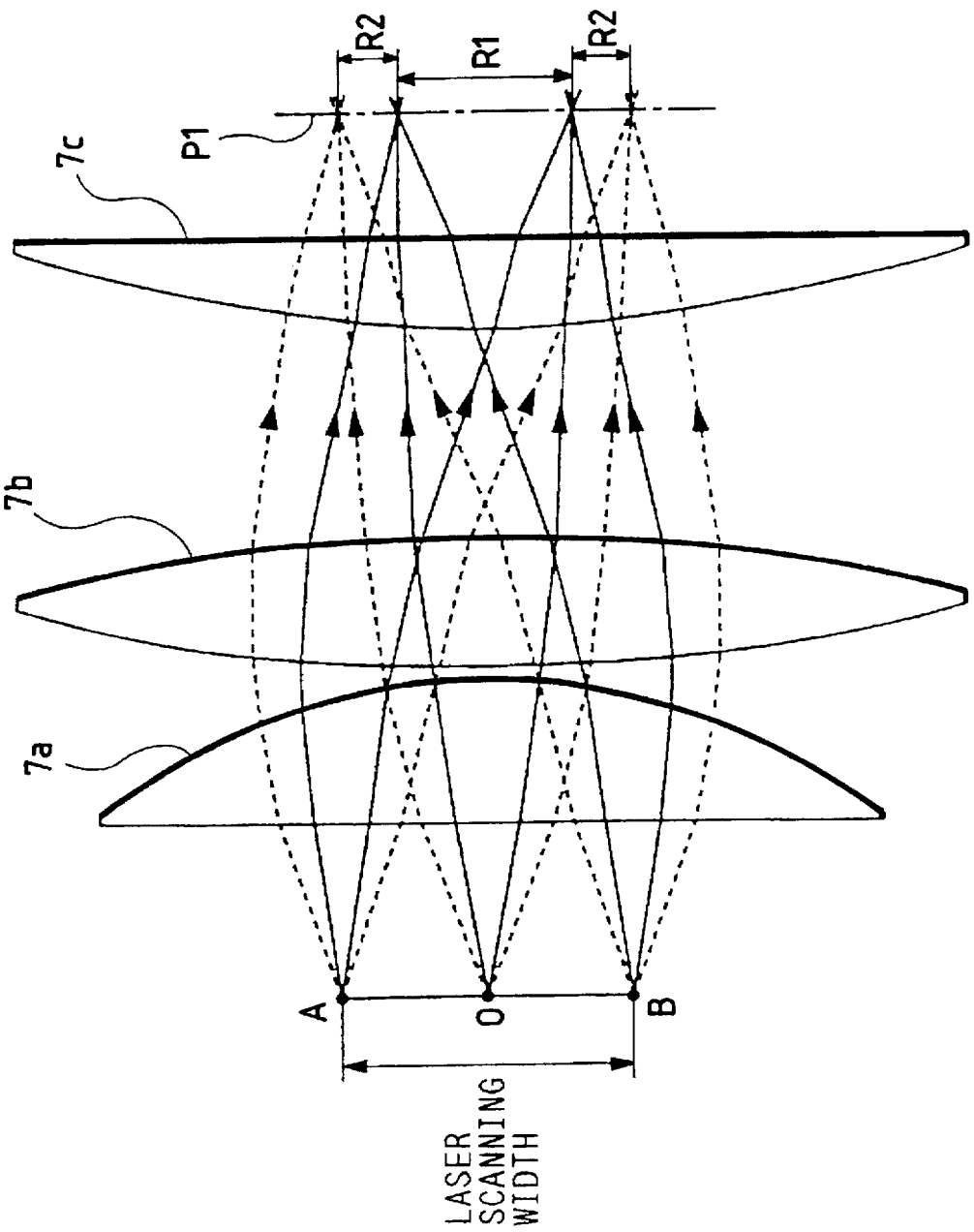

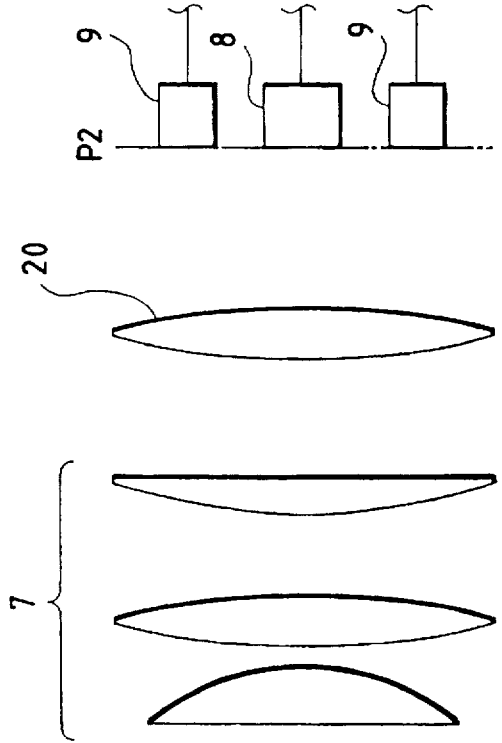
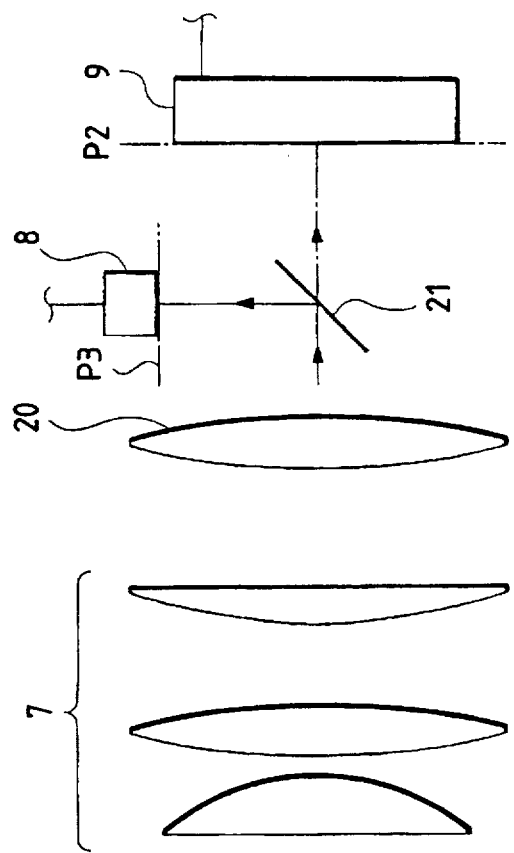
FIG. 5A
FIG. 5B

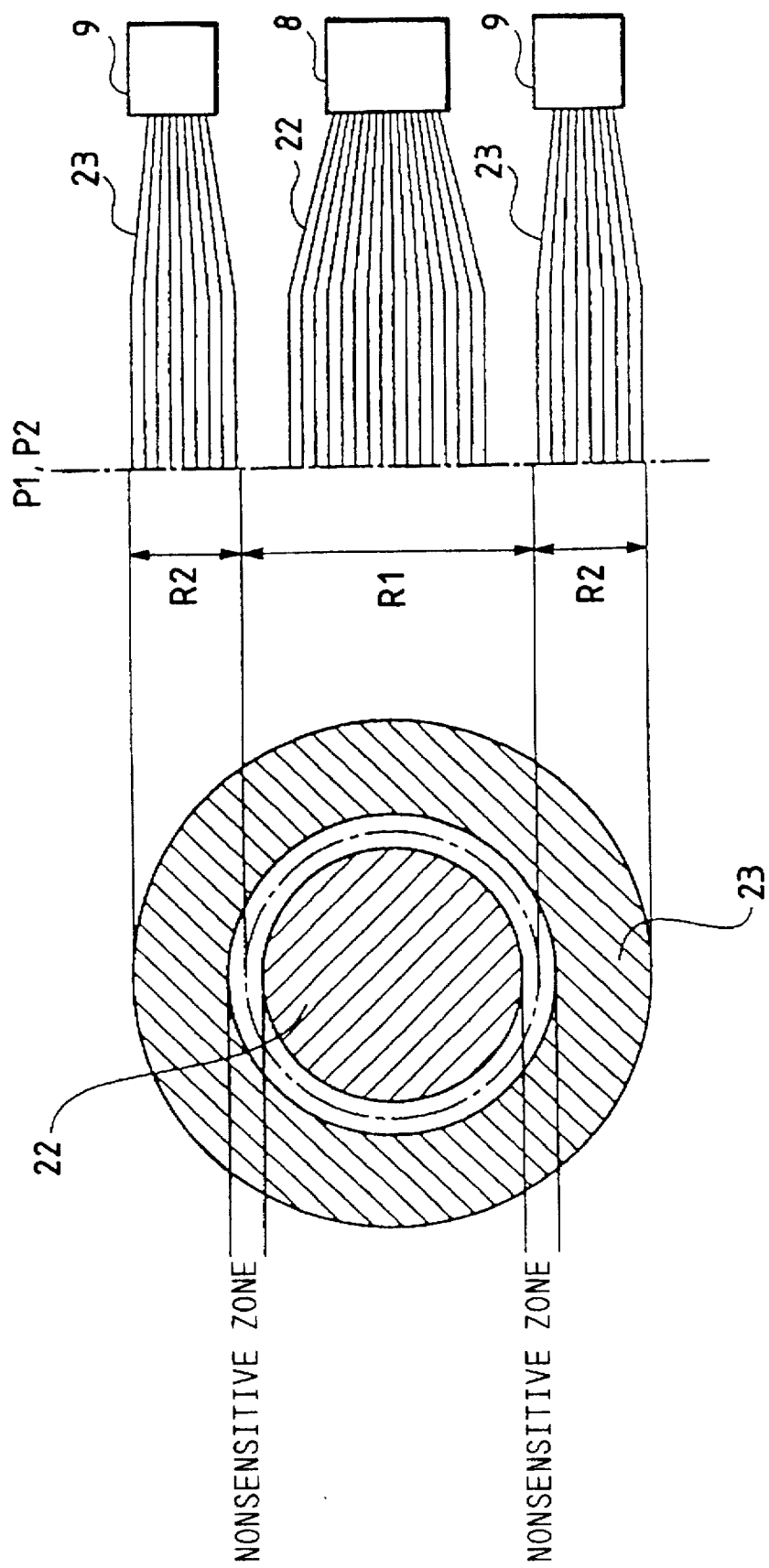

APPARATUS FOR INSPECTING SURFACE DEFECTS WITH REGULARLY REFLECTED LIGHT AND PERIPHERALLY SCATTERED LIGHT

This is a continuation of application Ser. No. 08/413,470, filed Mar. 28, 1995 now abandoned.

BACKGROUND OF THE INVENTION

1. Field of the Invention

The present invention relates to a defect inspecting apparatus for inspecting a defect of, for instance, an etched product of a leadframe, a shadow mask or the like, or a strip steel sheet, in which light is emitted towards an object to be inspected, and a defect of the object to be inspected is detected on the basis of the light reflected therefrom.

2. Related Art

As defect inspecting apparatuses or methods, the following have hitherto been proposed.

(1) A method of detecting a defect of a metal object surface wherein a surface defect is detected with high accuracy on the basis of a high S/N ratio by such as specifying an angle formed by the incident direction of emitted light and the surface to be inspected to a particular range as disclosed in Unexamined Japanese Patent Application No. Sho. 58-204351.

(2) A surface inspecting apparatus in which there are provided a photoelectric converter for receiving regularly reflected components of light reflected from an object to be inspected and a photoelectric converter for receiving irregularly reflected components, and a defect signal is enhanced by subtracting a signal output from the photoelectric converter for the irregularly reflected light from a signal outputting from the photoelectric converter for the regularly reflected light, as disclosed in Unexamined Japanese Patent Application No. Hei. 5-188010.

However, the apparatus of type (1) above performs inspection by taking note of only the regularly reflected light of the light reflected from the object to be inspected, and no consideration is given to anisotropically reflected light which is irregularly reflected from a defective portion in various directions. Accordingly, in a case where characteristics of the defective portion do not appear noticeably, there is a possibility of the defect being overlooked.

In addition, as for the apparatus of type (2) above, although a signal in which irregularly reflected light is subjected to photoelectric conversion is used, since only part of the irregularly reflected light is detected, there is room for improvement.

SUMMARY OF THE INVENTION

The present invention was made in view of the above-described deficiencies, and its object is to provide a defect inspecting apparatus which is capable of more completely evaluating the light reflected from the object to be inspected, and of detecting a defect of the object to be inspected with high accuracy.

To attain the above object, in accordance with the present invention, there is provided a defect inspecting apparatus in which light is emitted to an object to be inspected, and a defect of a surface of the object to be inspected is inspected on the basis of light reflected therefrom, the defect inspecting apparatus comprising: a focusing lens for focusing virtually all the reflected light; a first light-receiving member for detecting a quantity of light in a regularly reflected light region of the reflected light in a vicinity of a plane where an image is formed by the focusing lens; a second light-receiving member for detecting a quantity of light in a peripherally scattered light region of the reflected light in the vicinity of the plane where the image is formed by the focusing lens; first comparing means for comparing the quantity of light detected by the first light-receiving member and a first threshold value; second comparing means for comparing the quantity of light detected by the second light-receiving member and a second threshold value; and determining means for determining the presence or absence of a defect on the surface of the object to be inspected on the basis of results of comparison by the first comparing means and the second comparing means.

Preferably, the determining means determines that a defect is present when the quantity of light detected by the first light-receiving member is smaller than the first threshold value, and the quantity of light detected by the second light-receiving member is larger than the second threshold value.

Further, reflecting means for reflecting the regularly reflected light is preferably provided between the focusing lens and the light-receiving members.

Furthermore, a relay lens for allowing the image formed by the focusing lens to be formed on a further reduced scale is disposed between the focusing lens and the light-receiving members.

Moreover, reflecting means for reflecting the regularly reflected light is preferably disposed between the relay lens and the light-receiving members.

Furthermore, a diffusion plate is preferably disposed between the focusing lens and the relay lens.

Additionally, it is preferred that a first transmitting means for receiving the light incident upon the central, regularly reflected light region and transmitting the same to the first light-receiving member be disposed between the image-forming plane and the first light-receiving member, and that a second transmitting means for receiving the light incident upon the peripheral scattered light region and transmitting the same to the second light-receiving member be disposed between the image-forming plane and the second light-receiving member.

In addition, preferably, there is provided a defect inspecting apparatus in which light is emitted to an object to be inspected, and a defect of a surface of the object to be inspected is inspected on the basis of light reflected therefrom, the defect inspecting apparatus comprising: a focusing lens for focusing virtually all the reflected light; a first light-receiving element for detecting a quantity of light in a regularly reflected light region of the reflected light in a vicinity of a plane where an image is formed by the focusing lens; a second light-receiving element for detecting a quantity of light in a peripherally scattered light region of the reflected light in the vicinity of the plane where the image is formed by the focusing lens; comparing means for subtracting the quantity of light detected by the second light-receiving element from the quantity of light detected by the first light-receiving element, and for comparing the differential signal and a threshold value; and determining means for determining the presence or absence of a defect on the surface of the object to be inspected on the basis of a result of comparison by the comparing means.

Virtually all the light reflected from the object to be inspected is focused by the focusing lens. Quantities of light in the regularly reflected light region and the peripherally scattered light region of the reflected light in the vicinity of the plane where an image is formed by the focusing lens are detected. The respective quantities of regularly and peripherally reflected light are compared with the first and second threshold values, and the presence or absence of a defect on the surface of the object to be inspected is determined on the basis of the result of comparison.

BRIEF DESCRIPTION OF THE DRAWINGS

FIG. 1 is a diagram illustrating an arrangement of a defect inspecting apparatus in accordance with an embodiment of the present invention;

FIGS. 2A and 2B are diagrams for explaining a state of light reflected from the object to be inspected;

FIGS. 4A and 4B are diagrams for explaining the operation of a focusing lens;

FIGS. 5A and 5B are diagrams illustrating a modification of the embodiment shown in FIG. 1;

FIGS. 6A and 6B are diagrams illustrating another modification of the embodiment shown in FIG. 1.

DESCRIPTION OF THE PREFERRED EMBODIMENTS

Figure 3:
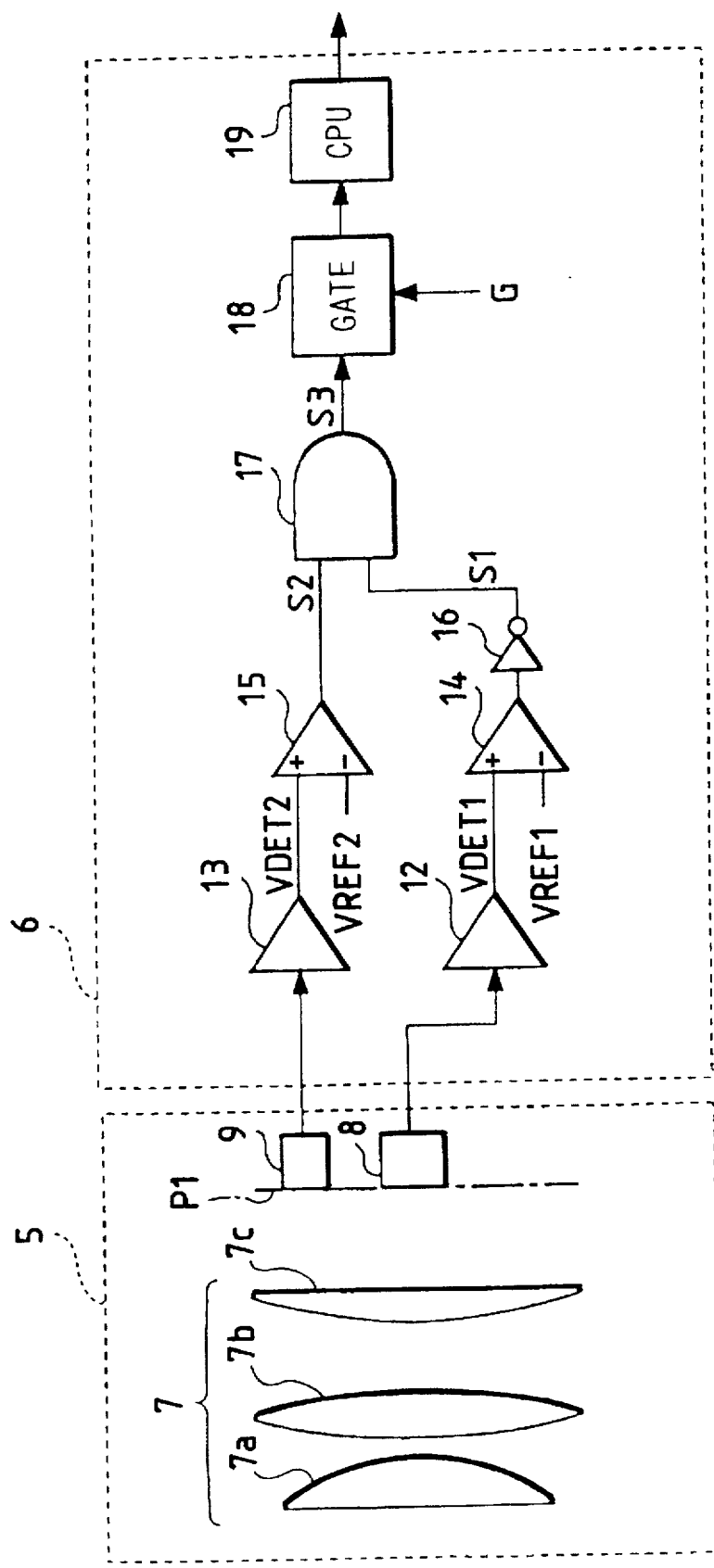
FIG. 3 is a diagram illustrating a specific configuration of a light-receiving unit and a determining unit shown in FIG. 1.

Referring now to the drawings, a description will be given of a preferred embodiment of the present invention.

FIG. 1 is a diagram schematically illustrating an arrangement of a defect inspecting apparatus in accordance with an embodiment of the present invention. This apparatus has as its principal component elements a laser light source 1 for emitting laser light; a polygonal mirror 2 which rotates at high speed and reflects the laser light; an fθ lens 3 for linearly focusing the laser light reflected by the polygonal mirror 2 onto an object 4 to be inspected; a light-receiving unit 5 which receives virtually all of the light reflected by the object 4 to be inspected, subjects the reflected light to photoelectric conversion, and outputs an electrical signal corresponding to a quantity of light received; a determining unit 6 for determining the presence or absence of a defect of the surface of the object to be inspected on the basis of the electrical signal inputted from the light-receiving unit 5.

It should be noted that a light source for scanning in the Y-direction is obtained by a combination of the laser light source 1, the polygonal mirror 2, and the fθ lens 3. In lieu of the Y-direction scanning light source, it is also possible to use an optical system including a linear light source having a width corresponding to the Y-direction width.

Incidentally, the object 4 to be inspected is placed on a table (not shown) which is capable of moving in the X-direction in the drawing.

In accordance with the arrangement shown in FIG. 1, the laser light emitted from the laser light source 1 is reflected by the polygonal mirror 2, and is focused and applied to the surface of the object to be inspected by means of the fθ lens. The laser light moves in the Y-direction on the object 4 to be inspected as the polygonal mirror 2 is rotated in the direction of the arrow in the drawing. Accordingly, as the object 4 to be inspected is moved in the X-direction, the overall surface of the object 4 to be inspected is scanned by the laser light.

Practically all the light reflected by the object 4 to be inspected, including not only the regularly reflected light but also the anisotropically reflected light which is irregularly reflected in various directions by a pit or the like in the object to be inspected, is made incident upon the light-receiving unit.

FIGS. 2A and 2B are diagrams for explaining the state of light reflected from the object 4 to be inspected. In FIG. 2A, it is assumed that the laser light is incident upon a straight line connecting points A and B, and P0 represents an imaginary light-receiving surface. For instance, the light made incident upon the point A in FIG. 2A is reflected as regularly reflected light indicated by the solid line and peripheral scattered light included in a range indicated by the broken line in the vicinity thereof. The same holds true of the light made incident upon the point B. Accordingly, on the imaginary light-receiving surface P0, the reflected light from the points A and B is detected in the range indicated by the broken lines, and the distribution of the light intensity is shown in FIG. 2B. As shown in FIG. 2B, the solid lines indicate the light intensity distributions of the small reflection angle scattered light, that is, the regularly reflected light, from the points A and B, respectively, while the broken lines indicate the light intensity distributions of the large reflection angle scattered light, that is, the peripherally scattered light, from the points A and B. As is apparent from this drawing, the regularly reflected light assumes a sharp distribution in which a peak value is very high, while the peripheral scattered light assumes a gentle distribution in which a peak value is comparatively small.

The regularly reflected light from the entire straight line AB connecting the points A and B is detected in a region (regularly reflected light region) which is indicated by being hatched in FIG. 2A, while the peripheral scattered light from the entire straight line AB is detected in a region (peripheral scattered light region) surrounded by the dot-dashed line. It should be noted that although the dot-dashed line actually overlaps partially with the broken lines, the dot-dashed line is slightly offset for the purpose of explanation.

FIG. 3 is a diagram which specifically illustrates the configuration of the light-receiving unit 5 and the determining unit 6. The light-receiving unit 5 has as its principal component elements a focusing lens 7 consisting of convex lenses 7a, 7b, and 7c, a first photodiode (first light-receiving element as a first light-receiving member) 8 for detecting a quantity of light (light intensity) on an image-forming plane P1 of the focusing lens 7, and a second photodiode 9 (a second light-receiving element as a second light-receiving member) having a light-receiving region surrounding the same. Incidentally, as the second photodiode 9, a multiplicity of photodiodes may be disposed around the first photodiode 8.

FIGS. 4A and 4B are diagrams for explaining the operation of the focusing lens 7, in which the regularly reflected light and peripherally scattered light from the points AOB on the straight line are indicated by the solid lines and broken lines, respectively. As is apparent from this drawing, the regularly reflected light and peripherally scattered light from the straight line AOB are focused by the focusing lens 7, and the range indicated by R1 on the image-forming plane P1 becomes the regularly reflected light region, while the range indicated by R2 becomes the peripheral scattered light region. When the image-forming plane P1 is viewed from the right-hand side in the drawing, the regularly reflected light region R1 and the peripheral scattered light region R2 shown in FIG. 4B.

Returning to FIG. 3, the first photodiode (first light-receiving element) 8 is disposed so as to detect the quantity of light in the regularly reflected light region, and its output is connected to a non-inverted input of a first comparator 14 via an amplifier 12. Meanwhile, the second photodiode (second light-receiving element) 9 is disposed so as to detect the quantity of light in the peripherally scattered light region, and an output of the diode 9 is connected to a non-inverted input of a second comparator 15 via an amplifier 13. Incidentally, in a case where the second photodiode 9 is constituted by a multiplicity of photodiodes 9, an arrangement is adopted such that their outputs are connected to an adder, and its output is connected to the amplifier 13.

First and second reference voltages (first and second threshold values) VREF1 and VREF2 are supplied to inverted inputs of the first and second comparators 14 and 15, respectively. An output from the first comparator 14 is connected to an input of an AND circuit 17 via an inverter 16, while an output from the second comparator 15 is directly connected thereto. An output from the AND circuit 17 is connected to a CPU (central processing unit) 19 for controlling the overall apparatus via a gate circuit 18. An output from the CPU 19 is connected to a display unit, a defective-product sorter, and the like which are not shown. In addition, a gate signal G for allowing only a signal concerning an inspecting region of the object 4 to pass is supplied to the gate circuit 18. This gate signal is generated on the basis of, for instance, a signal representing the rotational phase of the polygonal mirror 2. Alternatively, a signal may be output in synchronism with an appropriately selected timing of a start or end, or the like, of the movement of the table or the reading of data, and this signal may be used as the gate signal.

Next, a description will be given of the operation of the configuration shown in FIG. 3.

A voltage signal corresponding to the quantity of light detected in the regularly reflected light region is output from the first photodiode 8, is amplified by the amplifier 12, and is input to the first comparator 14 (VDET1). Meanwhile, a voltage signal corresponding to the quantity of light detected in the peripherally scattered light region is output from the second photodiode 9, is amplified by the amplifier 13, and is input to the second comparator 15 (VDET2). Here, in a case where the quantity of light detected in the regularly reflected light region is small, and if VDET1<VREF1 holds, the output from the first comparator 14 is at a low level, while if, conversely, VDET1>VREF1 holds, the output from the first comparator 14 is at a high level. The same holds true of the second comparator 15. Its output signal S2 is at the low level when VDET2<VREF2 holds, and at the high level when VDET2>VREF2 holds. Meanwhile, an output signal S1 from the inverter 16 is at the low or high level in correspondence with the high or low level of the output from the first comparator 14. Accordingly, the relationships between the quantities of light received by the photodiodes 8 and 9 on the one hand, and their signals S1 and S2 and the output signal S3 from the AND circuit 17 on the other, are shown below. It should be noted that the high level is set at "1," while the low level is set at "0."

(1) If the quantity of light in the regularly reflected light region is small (VDET1<VREF1), and the quantity of light in the peripheral scattered light region is large (VDET2>VREF2),

S1=1, S2=1, S3=1

(2) If the quantity of light in the regularly reflected light region is large (VDET1>VREF1), and the quantity of light in the peripheral scattered light region is small (VDET2<VREF2),

S1=0, S2=0, S3=0

(3) If the quantity of light in the regularly reflected light region is large (VDET1>VREF1), and the quantity of light in the peripheral scattered light region is large (VDET2>VREF2),

S1=0, S2=1, S3=0

(4) If the quantity of light in the regularly reflected light region is small (VDET1<VREF1), and the quantity of light in the peripheral scattered light region is small (VDET2<VREF2),

S1=1, S2=0, S3=0

The CPU 19 determines that a defect is present on the object 4 to be inspected if the output signal from the AND circuit 17 S3=1 (case (1) above), i.e., if the quantity of light in the regularly reflected light region is small, and the quantity of light in the peripheral scattered light region is large. This is because when a defect such as a pit or the like is present on the surface of the object to be inspected, the quantity of light received in the regularly reflected light region decreases, and the quantity of light received in the peripherally scattered light region increases.

It should be noted that the value of VREF1 and the value of VREF2 are determined such that the states of (3) and (4) above do not normally occur.

If it is determined that a defect is present, a defect determination signal is output by the CPU 19, and the operations of selecting the defective product, and the like are carried out.

As described above, in this embodiment, since virtually all the light reflected from the object 4 to be inspected is focused and an image thereof is formed by the focusing lens 7, and a defect is determined on the basis of the quantities of light in both the regularly reflected light region and the peripherally scattered light region in the image-forming plane P1, it is possible to prevent overlooking a defect and to improve the inspection accuracy.

In addition, in a case where a determination is made on the basis of, for instance, only the quantity of light received in the regularly reflected light region, if the first reference voltage VREF1 is made excessively high, in a portion where the background of the object 4 to be inspected changes (e.g., in a portion where a stain or a change in color is present), part of the incident light is absorbed without being reflected. Even if the light is reflected, this part of the incident light is diffused and the quantity of the reflected light decreases, and there is a possibility of this being erroneously determined as being a defect. On the other hand, if the VREF1 value is made excessively low, the possibility of overlooking a defect increases, so that it is necessary to set the reference voltage VREF1 with high accuracy when detecting defects with only regularly reflected light.

By contrast, in this embodiment, the quantities of light not only from the regularly reflected light region but also from the peripherally scattered light region are taken into consideration. The quantity of light received in the peripherally scattered light region does not decrease significantly even in the portion where the background changes, so that the accurate setting of the reference voltage VREF1 does not constitute a major problem. That is, even in a case where the first reference voltage VREF1 is set to a relatively high level so that VDET1<VREF1 holds when the quantity of light drops due to a change in the background, it is possible to detect accurately a defective product by determining the presence or absence of the defect depending on whether or not the AND condition with the determination based on the quantity of light in the peripherally scattered light region is met.

In addition, in this embodiment, complicated calculations such as a comparison between the object to be detected on the one hand, and CAD data and data on a photographed acceptable product on the other, is not required. A defect can be detected by only the processing of analog signals, so that it is possible to detect a defect at high speed and with high accuracy in a simple arrangement.

Figure 7:
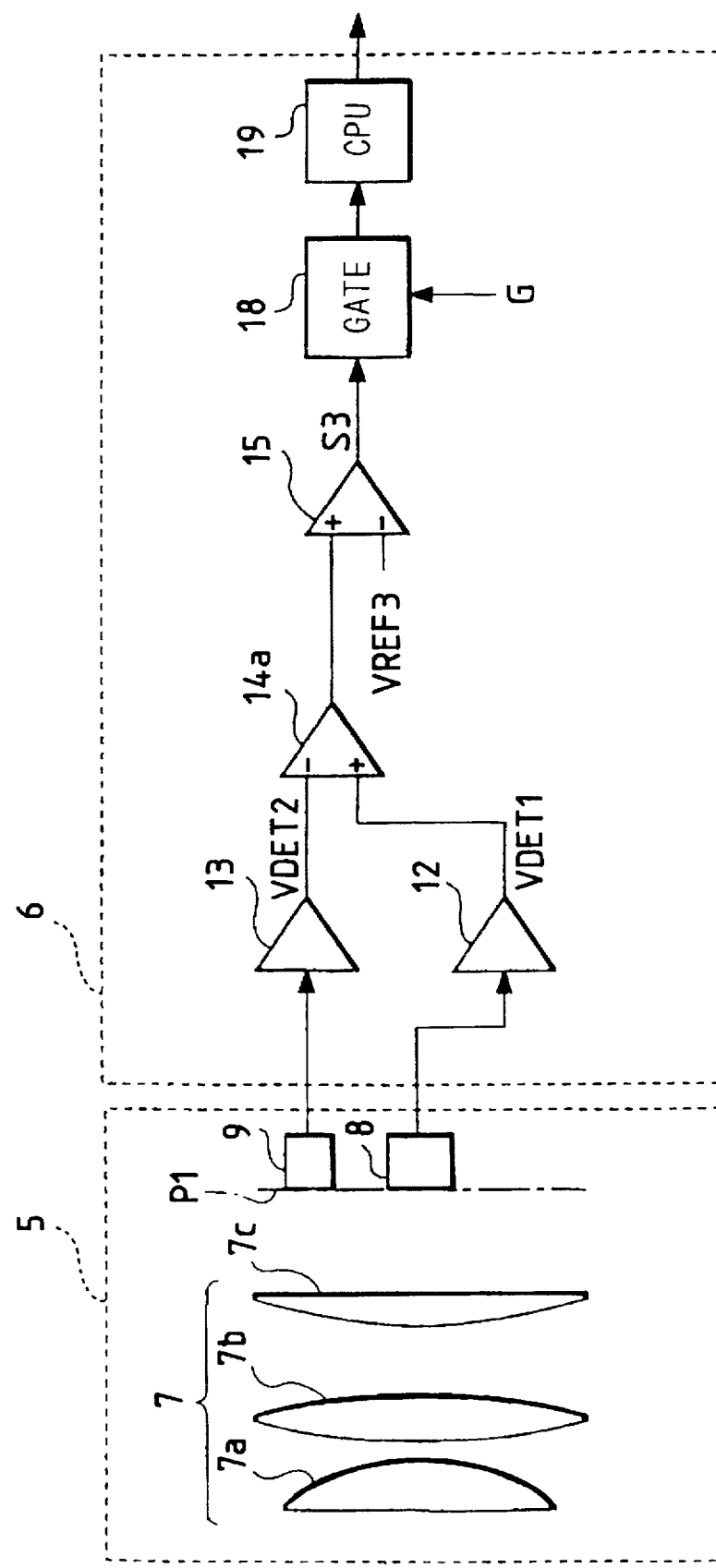
FIG. 7 is a diagram showing an arrangement of a light-receiving unit and a determination unit.

It should be noted that in the configuration shown in FIG. 3, the positions of the photodiodes 8 and 9 need not necessarily be aligned with the image-forming plane P1, and it suffices if the photodiodes 8 and 9 are disposed in the vicinity of the image-forming plane P1. In addition, as for the configuration of the light-receiving unit 5 and the determining unit 6, an arrangement may be provided as shown in FIG. 7, in which the output from the amplifier 12 is connected to the non-inverted input of the first comparator 14a, the output from the amplifier 13 is connected to the inverted input of the first comparator 14a, the output from the first comparator 14a is connected to the non-inverted input of the second comparator 15, the reference voltage VREF3 is supplied to the inverted input of the second comparator 15, and the output from the second comparator 15 is connected to the gate 18. Additionally, with reference to FIG. 3, an arrangement may be provided such that the output from the amplifier 12 is connected to the inverted input of the first comparator 14, the reference voltage VREF1 is supplied to the non-inverted input thereof, and the inverter 16 is omitted.

Furthermore, as for the configuration of the light-receiving unit 5 and the determining unit 6, an arrangement may be provided as shown in FIG. 7, in which the output from the amplifier 12 is connected to the non-inverted input of a differential amplifier 14a, the output from the amplifier 13 is connected to the inverted input of the differential amplifier 14a, the output from the differential amplifier 14a is connected to the inverted input of the comparator 15, a reference voltage VREF3 is supplied to the non-inverted input of the comparator 15, and the output from the comparator 15 is connected to the gate 18. According to this embodiment, by selecting the reference voltage VREF3 to an appropriate value, a signal S3 becomes "0," when a defect is present, and the signal S3 becomes "1" when a defect is not present.

In addition, the focusing lens 7 may be preferably constituted by a combination of convex lenses with also at least one meniscus lens or at least one concave lens, for example, or it is also possible to use a Fresnel lens.

Furthermore, as shown in FIG. 5A, an arrangement may be provided such that a relay lens 20 (in FIG. 5A, an example of only one relay lens is illustrated), which is formed by a convex lens or by combining a plurality of convex lenses or the like, is disposed between the focusing lens 7 and the photodiodes 8 and 9, so as to form an image on the image-forming plane P2 by further reducing the image due to the focusing lens 7. Alternatively, a Fresnel lens may be used in the same way for the focusing lens.

Furthermore, as shown in FIG. 5B, an arrangement may be provided such that a mirror 21 which reflects only the light reflected in the regularly reflected light region is disposed between the relay lens 20 and the photodiode 9, and the photodiode 8 is disposed at a distance which is equivalent to the distance from the mirror surface on the optical path of the reflected light to a plane P2. In this arrangement, the photodiode 9 serving as the second light-receiving element need not be formed to be not provided with a light-receiving region at a portion corresponding to the regularly reflected light region, so that it is possible to form a relatively inexpensive one.

Furthermore, in FIG. 5B, an arrangement may be provided in which the photodiode 8 is omitted. In this arrangement, since the input signal of the amplifier 12 becomes 0, the signal S1 in FIG. 3 is always "1," but the signal S2 becomes "1" only when a defect is present, so that it is possible to determine that a defect is present when the signal S3=1. Incidentally, in this arrangement, it is possible to omit the amplifier 12, the comparator 14, the inverter 16, and the AND circuit 17. Additionally, in FIG. 5B, an arrangement may be provided in which the relay lens 20 is omitted.

Furthermore, in the case where the focusing lens 7 and the relay lens 20 are used, an arrangement may be provided such that a diffusion plate (a ground glass plate) for diffusing the transmitted light rays is inserted between the two lenses. If the diffusion plate is provided, part of the transmitted light is scattered outwardly, the quantity of light decreases, but some of the light undergoes large refraction unobtainable by a normal lens, so that the relay lens which is provided in a subsequent stage can be made a relatively inexpensive small lens instead of an expensive large lens.

Furthermore, as shown in FIG. 6, an arrangement may be provided such that there is provided an optical fiber bundle 22 as a first transmitting means having an end face in the regularly reflected light region R1 on the plane P1 or P2 where the image is formed by the focusing lens 7 or the relay lens, and there is provided an optical fiber bundle 23 as a second transmitting means having an end face in the peripheral scattered light region R2, so as to introduce the reflected light to the photodiodes 8 and 9, respectively. Incidentally, FIG. 6B is a diagram in which the image-forming plane P1 (or P2) is viewed from the left-hand side. By virtue of this arrangement, it is possible to detect a defect by using a quantity of light over the entire regions of the regularly reflected light region R1 and the peripherally scattered light region R2 (i.e., a quantity of light obtained by integrating the entire regions), thereby making it possible to further improve the inspection accuracy.

It should be noted that the photoelectric conversion elements (light-receiving elements) are not confined to photodiodes, and it is possible to use photodiode arrays, photomultipliers, CCDs or the like.

In addition, an arrangement may be provided such that two sets of the above-described optical systems are respectively disposed in a face-to-face relationship to the upper and lower surfaces of the object to be inspected, so as to simultaneously inspect both surfaces of the object to be inspected. In this case, with respect to the arrangement up to a stage for obtaining the incident light (e.g., the laser light source 1, the polygonal mirror 2, and the fθ lens 3), all the elements may not necessarily be provided in two sets, and an arrangement may be provided such that one linear light source is branched off into two optical paths by means of an appropriate optical system (a combination of a half mirror for dividing the incident light into two and a mirror for changing the direction), so as to be made incident upon the two surfaces.

As described above, in accordance with the present invention, virtually all of the light reflected from the object to be inspected is focused by the focusing lens, the quantities of light in the regularly reflected light region and the peripherally scattered light region of the reflected light in the vicinity of the plane of an image formed by the focusing lens are detected, the respective detected quantities of light are compared with the first and second threshold values, and the presence or absence of a defect of the surface of the object to be inspected is determined on the basis of the result of comparison. Accordingly, it is possible to determine a defect on the basis of the light intensity distribution of virtually all the light reflected from the object to be inspected, so that it is possible to improve the defect detection accuracy.

What is claimed is:

1. A defect inspection apparatus for inspecting a surface defect of an object, comprising:

a light emitting device for emitting a light towards the object to linearly scan the object;

a light receiving unit for receiving a reflected light from the object, the reflected light containing a regularly reflected light and a peripherally scattered light, the light receiving unit comprising:

a focusing lens for focusing the regularly reflected light on a center region in an image-forming plane and the peripherally scattered light on a peripheral region which spreads concentrically outside the center region;

a first light-receiving member for receiving said regularly reflected light in said center region and for converting a quantity of the regularly reflected light in the image-forming plane to a first electric signal; and a second light-receiving member for receiving said peripherally scattered light in said peripheral region, and for converting a quantity of the peripherally scattered light in the image-forming plane to a second electric signal; and a determining unit for determining the surface defect in accordance with the first electric signal and the second electric signal, the determining unit comprising:

a comparing section for comparing the first electric signal with the second electric signal to generate a comparison signal; and a determining section for determining a presence of the surface defect in accordance with the comparison signal.

2. The defect inspection apparatus of claim 1, wherein said second light-receiving member converts the quantity of the peripherally scattered light on the whole of the peripheral region into the second electric signal.

3. The defect inspection apparatus of claim 1, wherein the light receiving unit further comprises a reflecting mirror disposed between the focusing lens and both of the first and second light-receiving members in an optic axis of the reflected light, the reflecting mirror reflecting the regularly reflected light in a direction substantially perpendicular to the optic axis.

4. The defect inspection apparatus of claim 1, wherein the light receiving unit is disposed at a single position which is located opposite to the light emitting device with respect to the object in a plan view.

5. The defect inspection apparatus of claim 1, wherein the determining unit further comprises an amplifying section for amplifying the first electric signal and the second electric signal, the amplifying section having an amplification such that the first electric signal and the second electric signal are the same value when the object has either a defect or no defect.

6. The defect inspection apparatus of claim 5, wherein the comparing section generates the comparison signal when the second electric signal differs from the first electric signal.

7. The defect inspection apparatus of claim 1, wherein the first light-receiving member comprises a plurality of light-receiving elements.

8. The defect inspection apparatus of claim 1, wherein the second light-receiving member comprises a plurality of light-receiving elements.

9. The defect inspection apparatus of claim 1, wherein said second light-receiving member includes a photodiode having a light-receiving region surrounding said first light-receiving member.

10. The defect inspection apparatus of claim 1, wherein said second light-receiving member includes a multiplicity of photodiodes which are disposed around said first light-receiving member.

* * * * *